(12) United States Patent
Chappell et al.

(10) Patent No.: US 9,795,810 B2
(45) Date of Patent: Oct. 24, 2017

(54) PROPYLENE GLYCOL/GLYCERIN-BASED DEODORANT (75) Inventors: Christopher T. Chappell, Petaluma, CA (US); Stefan Gafner, Kennebunkport, ME (US); Anne Gale, Landing, NJ (US); Nick Holerca, Somerset, NJ (US); Jennifer L. Lafrance, Biddeford, ME (US); Steve Misner, Verona, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 420 days.

(21) Appl. No.: 12/681,308

(22) PCT Filed: Sep. 30, 2008

(86) PCT No.: PCT/US2008/078272
§ 371 (c)(1),
(2), (4) Date: Apr. 1, 2010

(87) PCT Pub. No.: WO2009/046008
PCT Pub. Date: Apr. 9, 2009

(65) Prior Publication Data
US 2010/0254926 A1    Oct. 7, 2010

Related U.S. Application Data (60) Provisional application No. 60/997,119, filed on Oct. 1, 2007.

(51) Int. Cl.
*A61Q 15/00* (2006.01)
*A61K 8/02* (2006.01)
*A61K 8/28* (2006.01)
*A61K 8/34* (2006.01)

(52) U.S. Cl.
CPC ............ *A61Q 15/00* (2013.01); *A61K 8/0229* (2013.01); *A61K 8/28* (2013.01); *A61K 8/345* (2013.01)

(58) Field of Classification Search
CPC ........ A61K 8/0229; A61K 8/28; A61K 8/345; A61Q 15/00
See application file for complete search history.

(56) References Cited

U.S. PATENT DOCUMENTS

| | | | |
|---|---|---|---|
| 3,943,242 A | 3/1976 | Fogel | |
| 3,996,346 A | 12/1976 | Staffier et al. | |
| 4,919,934 A | 4/1990 | Deckner et al. | |
| 5,256,405 A * | 10/1993 | Chappell ................ | A61K 8/375 424/195.15 |
| 5,260,053 A | 11/1993 | Chappell et al. | |
| 5,650,142 A | 7/1997 | Bergmann | |
| 5,650,143 A | 7/1997 | Bergmann | |
| 5,688,495 A | 11/1997 | Rosen et al. | |
| 6,001,342 A | 12/1999 | Forestier et al. | |
| 6,177,066 B1 | 1/2001 | Pataut et al. | |
| 6,403,072 B1 | 6/2002 | Scavone | |
| 6,475,473 B1 | 11/2002 | Perring | |
| 6,531,119 B1 | 3/2003 | Hall-Puzzio et al. | |
| 6,649,153 B1 | 11/2003 | Parekh et al. | |
| 6,793,915 B1 | 9/2004 | Guenin et al. | |
| 7,033,579 B1 | 4/2006 | Scavone | |
| 7,128,901 B2 | 10/2006 | Jonas et al. | |
| 2003/0139478 A1 | 7/2003 | Harper | |
| 2003/0235545 A1 | 12/2003 | Gueninn et al. | |
| 2004/0175346 A1 | 9/2004 | Guenin et al. | |
| 2004/0247545 A1 | 12/2004 | Jonas et al. | |
| 2005/0048013 A1 | 3/2005 | Diec et al. | |
| 2005/0089488 A1 | 4/2005 | Kim | |
| 2006/0165623 A1 | 7/2006 | Workman et al. | |

FOREIGN PATENT DOCUMENTS

| | | |
|---|---|---|
| EP | 0107330 | 5/1984 |
| EP | 0 447 142 A | 9/1991 |
| EP | 2170257 | 4/2010 |

OTHER PUBLICATIONS

Office Action in corresponding Russian Patent Application No. 2010117168, dated Mar. 2, 2011.

* cited by examiner

*Primary Examiner* — Robert Cabral (57) ABSTRACT

The present invention relates to a stick type composition comprising propylene glycol, glycerin and water.

22 Claims, 5 Drawing Sheets

PROPYLENE GLYCOL/GLYCERIN-BASED DEODORANT

CROSS REFERENCE TO RELATED APPLICATIONS

This application claims priority to U.S. Application Ser. No. 60/997,119, filed on 1 Oct. 2007, which is incorporated herein by reference.

BACKGROUND OF THE INVENTION

Deodorants are traditionally used to reduce or eliminate body odor caused by the breakdown and fermentation of secretions from apocrine sweat glands. Gram positive bacteria such as *Corynebacterium xerosis*, and *Staphylococcus epidermis* are primary examples of odor causing bacteria that inhabit human skin. Many commercially available deodorants help to eliminate body odor by acting as a bactericide or bacteriostat. Bactericides kill bacteria while bacteriostats inhibit the growth of bacteria.

Commercially available underarm deodorants are available in several formats for application to the underarm area. Among these formats are aerosol, pump spray, roll-on, deodorant pads and stick applicators. Stick applicators are the most popular format followed by aerosols and pump sprays.

Stick applicators are essentially made of a solid or semi-solid material (i.e., a base composition that is firm to the touch) impregnated with ingredients that function to kill bacteria or limit their growth, fragrances, stabilizers, moisturizers, etc. To use the stick applicator, the user swipes the stick applicator in the armpit one or more times thereby coating the underarm with a thin layer of the deodorant material. As would be expected, there are characteristics that make some carrier materials superior to others. For example, product hardness, moisture content, stickiness, oiliness, wetness, easy by which the deodorant material goes on to the underarm (payout) and ease of application (e.g., how much pressure does the user have to use to deposit the required amount of deodorant material to the underarm referred to herein as "glide"), the ability of the deodorant material to stay on the underarm skin and hair and resist coming off (retention), visibility of deodorant residue on skin and clothing (visible residue), staining of clothing, irritation and inflammation of the skin, flow resistant to body heat (i.e., the deodorant composition material does not "drip" or "run" appreciably after application), etc.

Often, the base composition materials of deodorant sticks contain gelling agents, which are soluble in vehicle carriers. For example, the vehicle (solvent) is heated in order to dissolve the gelling agent in the vehicle and gelling occurs upon cooling of the composition. In particular, a gelling agent or agents may be selected from high melting point waxes (including beeswax, montan, ozokerite, ceresin, paraffin, synthetic waxes, hydrogenated castor oil); low melting point waxes (including fatty alcohols containing from about 8-20 carbons), and silicone waxes. A more particular group of gelling agents includes stearyl alcohol and hydrogenated castor oil.

For an overall discussion of gelling agents or thickening agents, attention is directed to the solidifying agents described in U.S. Pat. No. 4,919,934 to Deckner, et al., the contents of which have been incorporated herein by reference in their entirety. Examples of such thickening agents include crystalline waxes, cetyl stearate, stearyl stearate, cetyl myristate, cetyl palmitate, stearoxydimethicone, and microcrystalline waxes.

BRIEF DESCRIPTION OF THE DRAWINGS

The present invention will become more fully understood from the detailed description and the accompanying drawings, wherein.

BRIEF SUMMARY OF THE INVENTION

The present invention provides, in one aspect, underarm stick-type deodorants (deodorant compositions) that comprise one or more all-natural compounds to form a deodorant base composition. In another aspect, it is contemplated that the deodorant base compositions of the present invention are used as base compositions for cosmetic compositions such as lipstick and other facial and body cosmetics.

The compounds used to form a deodorant base composition function to distribute, protect and augment the effectiveness of the active and inactive ingredients of the deodorant composition which are impregnated in the deodorant base. In other words, a deodorant composition is made of a deodorant base composition that has been impregnated with the active and inactive ingredients of the deodorant product. The deodorant base compositions of the present invention feel essentially firm yet somewhat pliable. This type of formulation permits the application of the deodorant composition to the underarm area of the user by drawing the deodorant stick across the underarm area thereby transferring the product to the underarm area. In other words, the deodorant base composition of the present invention provides the user with a satisfactory skin feel, good glide properties, good payout and minimal residue. The deodorant base ingredients of the deodorant composition of the present invention have been selected to appeal to users by decreasing irritation occasionally associated with all-natural carrier compositions, improving effectiveness of the deodorant product and increasing user acceptance by improving the feel of the product on the skin.

In one embodiment, the deodorant base composition of the present invention comprises a formulation of propylene glycol, glycerin and water.

In one embodiment of the present invention, the deodorant base composition comprises about 20 to about 70 weight % propylene glycol, about 5 to about 60 weight % glycerin and about 10 to about 35 weight % water. In another embodiment of the present invention, the deodorant base composition comprises about 30 to about 60 weight % propylene glycol, about 10 to about 40 weight % glycerin and about 15 to about 30 weight % water. In another embodiment of the present invention, the deodorant base composition comprises about 35 to about 50 weight % propylene glycol, about 10 to about 30 weight % glycerin and about 17 to about 29 weight % water. In another embodiment, the deodorant base composition comprises about 47 to about 54 weight % propylene glycol, about 11 to about 22 weight % glycerin, and about 23 to about 28 weight % water.

DETAILED DESCRIPTION OF THE INVENTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

The present invention relates to all-natural stick-type deodorants and cosmetic compositions (especially underarm deodorants) wherein the deodorant base composition comprises a mixture of propylene glycol, glycerin and water in such ratios as to be effective for use as a stick-type deodorant and reduce or eliminate problems associated with all-natural deodorant stick base compositions. In another embodiment, the deodorant base also may comprise sodium stearate and other thickening agents or agents useful to improve skin feel, reduce irritation and/or inflammation or prevent excessive weeping or shrinkage of the final product.

The term "glide," as it applies to stick cosmetics and especially stick-type deodorants and as used herein, refers to the amount of friction that is generated upon application of the product.

The term "payout," as used herein, refers to the amount of material that is deposited on the user's body or test apparatus from the cosmetic or deodorant stick during the dispensing operation. In one embodiment, the deodorant base composition and deodorant composition give a satisfactory payout during the dispensing operation with normally exerted user pressure.

The terms "deodorant base composition(s)" and "deodorant composition(s)," as used herein, refer to compositions used to apply deodorant to a user's body, especially in the area of the underarm. The terms do not limit the product to delivering only deodorant materials and may also include, for example, antiperspirant materials in some embodiments. A "deodorant base composition" is a composition without deodorancy agents added. A "deodorant composition" is a deodorant base composition with deodorancy agents and, in certain embodiments, other agents added to achieve the desired user experience with the product.

The term "penetration," as used herein, is a measure of hardness. Penetration is determined, for example, by inserting a cone probe into the sample and measuring the amount of force used (e.g., in grams) with, for example, a Texture Technologies TA-XT2™ texture analyzer (Scarsdale, N.Y.).

In one embodiment of the present invention, the deodorant base composition comprises about 20 to about 70 weight % propylene glycol, about 5 to about 60 weight % glycerin and about 10 to about 35 weight % water. In another embodiment of the present invention, the deodorant base composition comprises about 30 to about 60 weight % propylene glycol, about 10 to about 40 weight % glycerin and about 15 to about 30 weight % water. In another embodiment of the present invention, the deodorant base composition comprises about 35 to about 50 weight % propylene glycol, about 10 to about 30 weight % glycerin and about 17 to about 29 weight % water.

In one embodiment, the weight ratio of propylene glycol: water:glycerin is about 2:1:1.

The present invention also relates to a stick-type deodorant made from the deodorant base of the present invention wherein the deodorant additionally comprises one or more of deodorancy agent(s), soothing agent(s), antioxidant(s) and fragrance(s).

The deodorant products of the present invention made from the deodorant base compositions of the present invention may also comprise one or more deodorancy ingredients. In an embodiment, the deodorancy ingredients have anti-microbial activity. The deodorant compositions of the present invention are not limited to any specific deodorancy ingredient or ingredients. In one embodiment, the deodorancy ingredient or ingredients are natural or all-natural. For example, in one embodiment, it is contemplated that the deodorant of the present invention also comprises one or more of hops extract, lemongrass oil or zinc ricinoleate, which are known in the art to reduce or inhibit the production of body odor. In another embodiment, the hops extract of the deodorant of the present invention is a $CO_2$ extract of, for example, the plant *Humulus lupulus*, more commonly known as the hop plant, or related strains and species of the plant known in the art. (See, e.g., co-pending U.S. patent application to S. Gafner, et al., U.S. Provisional Patent No. 60/997,118, which was filed concurrently [Oct. 1, 2007] with this application and which is herein incorporated by reference in its entirety).

The deodorant products of the present invention may also comprise other ingredients. For example, the deodorant of the present invention may comprise one or more ingredients for achieving and maintaining a desired consistency, one or more ingredients for giving the product a soothing skin feel, one or more antioxidants, one or more fragrances and one or more ingredients for fragrance duration or retention.

Non-limiting examples of ingredients suitable for use in achieving and maintaining desired consistency are, for example, caprylic capric triglyceride, glycerin, glyceryl laurate, water and sodium stearate.

Non-limiting examples of ingredients suitable for use as soothing agents are, for example, aloe vera leaf juice and other herbal extracts and witch hazel water.

Non-limiting examples of ingredients suitable for use as antioxidants are, for example, one or more of tocopherol and its derivatives, butyl hydroxyanisole (BHA), butyl hydroxytoluene (BHT), erythorbic acid, propyl gallate, sodium erythorbate, tertiary butyl hydroquinone (TBHQ), rosemary extract and, more preferably, ascorbic acid and salts thereof.

Non-limiting examples of ingredients suitable for use as fragrance are, for example, lemongrass oil, apricot fragrance, fir needle oil, lavandin oil and lavender oil.

Non-limiting examples of ingredients suitable for use for fragrance duration or longevity are silica shells.

In another embodiment, the deodorant of the present invention may comprise a "stick" formulation, a roll-on formulation or a spray formulation (e.g., as a pump spray), all of which the production is known in the art.

In one embodiment, one of the antimicrobial agents of the deodorant of the present invention is a $CO_2$ extract of, for example, the plant *Humulus lupulus*, more commonly known as the hop plant, or related strains and species of the plant known in the art.

In one embodiment, the present invention contemplates a deodorant product comprising a $CO_2$-extract of hops having anti-microbial, bacteriostatic and/or bactericidal properties. In this embodiment, the deodorant or body care product of the present invention comprises a $CO_2$ extract of hops at a concentration of about 0.001% to about 5% by weight. In another embodiment, the deodorant or body care product of the present invention comprises a $CO_2$ extract of hops at a concentration of about 0.05% to about 1% by weight. In another embodiment, the deodorant or body care product of the present invention comprises a $CO_2$ extract of hops at a concentration of about 0.1% to about 0.5% by weight.

In another embodiment, the body care and deodorant products of the present invention comprises an antioxidant compound. In one embodiment, the antioxidant compound is selected for one or more of tocopherol and its derivatives of about 0.001 to about 0.5 weight %, butyl hydroxyanisole (BHA) of about 0.0075 to about 0.1 weight %, butyl hydroxytoluene (BHT) of about 0.005 to about 0.02 weight %, erythorbic acid of about 0.05 to about 1 weight %, propyl gallate of about 0.01 to about 1 weight %, sodium erythorbate of about 0.05 to about 1 weight %, tertiary butyl hydroquinone (TBHQ) of about 0.005 to about 0.1 weight %, rosemary extract of about 0.02 to about 0.4 weight % and ascorbic acid and salts thereof of about 0.01 to about 0.1 weight %.

In another embodiment, the body care and deodorant products of the present invention comprises additional deodorizing compounds. In one embodiment, the compounds are selected from a group comprising various metal salts of an unsaturated carboxylic acid. In another embodiment the additional deodorizing compound is zinc ricinoleate. In another embodiment, the additional deodorizing compounds are also selected from glyceryl laurate and caprylic capric triglyceride both of about 0.1 to about 4 weight %, and lemongrass oil of about 0.01 to about 0.1 weight %.

In another embodiment, the body care and deodorant products of the present invention additionally comprises ingredients to improve the skin feel of the products of the present invention. For example, the present invention may comprise one or more of about 5-40 weight %, sodium stearate of about 0.5 to about 10 weight %, aloe extract or juice of about 0.5 to about 10 weight %, witch hazel (also known as witch hazel water) of about 1 to about 10 weight % and chamomile aqueous extract of about 1 to about 20 weight %.

In another embodiment, the body care and deodorant products are made up of one or more of the following: about 35% to about 70% by weight of a polyhydric alcohol; about 1.3% to about 6.5% by weight of a polyamine clarifier; about 1.3% to about 8% by weight of a $C_{14-22}$ fatty acid salt; about 0.5% to 4 weight % of an ester of glycerin and a $C_{8-18}$ fatty acid; and, optionally one or more ingredients selected from an herbal extract with anti-inflammatory or soothing properties; silicone copolyol; zinc pyridinethiol oxide; fragrance and color.

In another embodiment, the herbal extract of the present invention may be selected from one or more extracts of the following plants: *Aloe barbadensis* and other *Aloe* species, *Boswellia serrata, Calendula officinalis, Camellia sinensis, Curcuma longa, Curcuma xanthorrhiza, Glycyrrhiza glabra, Glycyrrhiza uralensis, Hamamelis virginiana, Mangifera indica, Matricaria recutita, Melissa officinalis, Rosmarinus officinalis, Scutellaria lateriflora, Scutellaria baicalensis, Thymus vulgaris, Thymus zygis, Uncaria tomentosa, Zingiber officinalis*.

In one embodiment, the polyhydric alcohol of the present invention is selected from the group consisting of organic compounds which contain about 2 to about 6 carbon atoms and about 2 to about 6 hydroxy groups. In another embodiment, the polyhydric alcohol is selected from the group consisting of ethylene glycol, propylene glycol, 1,3-propanediol, trimethylene glycol, butylene glycol, diethylene glycol, dipropylene glycol, glycerin, sorbitol, xylitol and mixtures thereof. In another embodiment, the polyhydric alcohol is propylene glycol or dipropylene glycol or a mixture thereof. The concentration of the polyhydric alcohol in the compositions of the present invention range from about 35% to about 70% by weight.

In another embodiment, the body care and deodorant products of the present invention, the polyamine is a homopolymer of units of structural formula (1), where $R_1$ is hydrogen or a $C_{1-3}$ alkyl group and n is an integer from 2-6, and the number of repeating units of structural formula (1) is, on average about 1450 to about 1550. Non-limiting examples of polyamines suitable for use in the present invention are described in U.S. Pat. No. 5,714,447 issued to Jones, et al., on Feb. 3, 1998 and U.S. Pat. No. 6,001,342 issued to Forestier, et al., on Dec. 14, 1999, both of which are incorporated herein by reference in their entirety.

In another embodiment, the body care and deodorant products of the present invention comprise a clarifier-surfactant selected from the group consisting of pentadoxynol-200, tetra(hydroxypropyl)diamine, 2-amino-2-methylpropanol, 2-amino-2-hydroxymethyl-1,3-propanediol, poly($C_{2-4}$ alkylene) glycol ethers of $C_{12-22}$ fatty alcohols in which the polyalkylene glycol portion contains from about 10 to about 100 alkyleneoxide repeating units. In another embodiment, the clarifier-surfactant is selected from the group consisting of laureth-10, laureth-20, laureth-30, laureth-40, PEG-10 Myristyl Ether, steareth-10, steareth-20, steareth-40, steareth-100, PEG-50 Stearyl Ether, steareth-100 and beheneth-20 and mixtures thereof. In another embodiment, the clarifier-surfactant is polyoxyethylene 3-pentadecyl phenyl ether. The concentration of the clarifier-surfactant in the compositions of the present invention is about 2% to about 3.5% by weight.

In another embodiment, the body care and deodorant products of the present invention comprise a fatty acid salt selected from alkali metal, alkaline earth metal, aluminum, and amine salts of $C_{14-22}$ fatty acids. In another embodiment, the $C_{14-22}$ fatty acid salt is selected from salts of myristic, palmitic, stearic, behenic, oleic, linoleic, and linolenic acids and mixtures thereof. In another embodiment, the $C_{14-22}$ fatty acid salt is selected from sodium stearate, potassium stearate, magnesium stearate, aluminum monostearate, sodium oleate, sodium palmitate, sodium behenate, diethylamine stearate, triethylamine stearate, and triethylemine oleate, and mixtures thereof. In one embodiment, the concentration of the $C_{14-22}$ fatty acid salt is about 2.2% to about 7% by weight. One purpose of the above agents is to thicken the deodorant so that it functions as a "stick-type" deodorant and are therefore referred to herein as thickening agents, gelling agents or structurants.

In another embodiment, the body care and deodorant products of the present invention comprise an ester of glycerin and a fatty acid selected from $C_{8-18}$ fatty acids. In another embodiment, the $C_{8-18}$ fatty acid is selected from caprylic, capric, lauric, myristic, palmitic, stearic, oleic, linoleic, and linolenic acids and mixtures thereof. In one embodiment, the concentration of the $C_{8-18}$ fatty acid ester in the compositions of the present invention is about 0.5% to about 4% by weight.

In one embodiment of the present invention, the deodorant base composition(s) and deodorant composition(s) of the present invention have an appearance consistent with the product appearing clear, essentially clear or non-visible when applied to the user's body. In this regard, the deodorant base composition(s) of the present invention may appear opaque or colored when formed into a shape consistent with a final deodorant product (e.g., shapes know in the art as used for stick-type deodorants) as long as the product is clear, essentially clear or non-visible when applied to the user's body in amounts consistent with typical use. In regards to other cosmetic compositions that are based on the deodorant base compositions of the present invention, it is contemplated that color compounds may be added.

The deodorant or deodorant base composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Where a softer product such as a gel or soft-solid composition is produced, the composition can be introduced into a dispensing package (for example, a package having a top surface with pores) as conventionally done in the art. Thereafter, the product can be dispensed from the dispensing package as conventionally done in the art, to deposit the active material, for example, on the skin. This provides good deposition of the active material on the skin. Other methods of producing a final deodorant product may include those taught in U.S. Pat. No. 7,128,901 to Jonas, et al., wherein the product the formed into a stick-like shape without the heating/melting step typical of these processes, or reasonable variations thereof.

The compositions of the present invention may be applied to the skin (especially underarm skin) using conventional techniques and stick applicators and in a manner that would result in typical loading as used for underarm products. For example, for use as deodorant and/or antiperspirant is, in certain embodiments, in an amount of about 0.5 to about 10 mg/cm$^2$, or about 2 to about 6 mg/cm$^2$, or about 4 mg/cm$^2$.

The invention will now be described below in the context of specific non-limiting examples. One skilled in the art will realize that variations of the present invention that differ somewhat from the examples given may be practiced without deviating from the teachings of the present invention.

EXEMPLIFICATION

Example 1

Comparison of Various PG/Glycerin Deodorant Bases

In this experiment five different formulations of deodorant base were made with the concentration of propylene glycol (PG) ranging from 0-70% by weight and the concentration of glycerin ranging from 0-70%. The ratios of PG to glycerin were 100:0, 75:25, 45:55, 15:85 and 0:100 with the PG:glycerin mixtures making up 70% by weight of the final deodorant base compositions. The final deodorant compositions were examined for clarity, weeping (i.e., formation of water droplets on the surface of the product after prolonged storage) and shrinkage of product. Additionally, pH of the product was determined as well as effectiveness at eliminating or reducing bacterial growth. pH is measured by making a 5% solution from the composition and then measuring the pH of the solution.

The deodorant compositions were made from stock formulations of the ingredients. The stock two formulations named Sodium Sterate/PG (propylene glycol)/glycerin pre-mix and PG/glycerin pre-mix were the only stock formulations that were varied between the different deodorant formulations. These formulations were the only ones to affect differences in the deodorant base composition. The stock formulations for Sodium Laureth 13-Carboxylate (SURFINE WLL™-70% solution), EDTA 2% solution, Methenamine/Sodium Acetate pre-mix, DI-Water and Fragrance remained the same throughout the deodorant base compositions. By mixing the five different Sodium Sterate/PG/Glycerin with the five different PG/Glycerin stock formulations at the same ratio for each test product formulations, the final concentrations of PG and Glycerin were easily changed without altering the final concentrations of the other ingredients in the deodorant base formulations.

The five final formulations each contained: 7 weight % Sodium Sterate; 0.3 weight % EDTA; 6.7 weight % Sodium Laureth 13-Carboxlyate (SURFINE WLL™); 14.2 weight % DI-Water; 0.3 weight % Sodium Acetate; 0.2 weight % Methenamine and 1.2 weight % Fragrance. In addition, each of the five formulations contained differing concentrations of PG and glycerin as follows: 69.7 weight % PG:0 weight % Glycerin; 52.3 weight % PG:17.4 weight % Glycerin; 31.4 weight % PG:38.3 weight % Glycerin; 10.5 weight % PG:59.2 weight % Glycerin and 0 weight % PG:69.7 weight % Glycerin.

Each of the formulations was tested for Compression, Loss of Weight and Visual Observations over a thirty (30) day period. Aging was performed at about 41° C. (105° F.).

The data are presented in Table 1, below.

TABLE 1

| PG:Glycerin | Sample # | Aging @ 40.6° C. (105° F.) (Days) | Compression | | Loss Weight | Observations |
|---|---|---|---|---|---|---|
| | | | F (g) | D (mm) | (cumm. g) | |
| 100:0 | 1 | 1 | 5211.3 | 6.824 | 0 | Clear |
| | 2 | 14 | 4980.6 | 7.522 | 1.98 | OK |
| | 3 | 14 | 5111.2 | 6.984 | 1.85 | OK |
| | 4 | 30 | 4823.1 | 5.542 | 3.05 | OK |
| | 5 | 30 | 5006.2 | 6.974 | 2.89 | OK |
| 75 to 25 | 1 | 1 | 4766.7 | 4.278 | 0 | Hazy |
| | 2 | 14 | 4511.2 | 4.544 | 2.12 | OK |
| | 3 | 14 | 4372.6 | 4.802 | 2.06 | OK |
| | 4 | 30 | 4504.3 | 4.397 | 3.46 | OK |
| | 5 | 30 | 4702.1 | 4.194 | 3.21 | OK |

TABLE 1-continued

| PG:Glycerin | Sample # | Aging @ 40.6° C. (105° F.) (Days) | Compression F (g) | D (mm) | Loss Weight (cumm. g) | Observations |
|---|---|---|---|---|---|---|
| 45 to 55 | 1 | 1 | 4251.3 | 5.244 | 0 | Hazy |
|  | 2 | 14 | 4377.4 | 4.948 | 2.04 | OK |
|  | 3 | 14 | 4506.1 | 5.422 | 1.92 | OK |
|  | 4 | 30 | 4237.8 | 5.164 | 3.14 | OK |
|  | 5 | 30 | 4458.6 | 4.885 | 3.3 | OK |
| 15 to 85 | 1 | 1 | 3351.2 | 7.856 | 0 | Not clear |
|  | 2 | 14 | 2841.5 | 9.243 | 2.56 | Water droplets |
|  | 3 | 14 | 3755.9 | 7.127 | 2.74 | Water droplets |
|  | 4 | 30 | 2566.2 | 9.344 | 4.28 | Shrinkage |
|  | 5 | 30 | 3884.1 | 6.985 | 4.62 | Shrinkage |
| 0 to 100 | 1 | 1 | 3542.1 | 7.645 | 0 | Not clear |
|  | 2 | 14 | 2747.5 | 9.205 | 2.41 | Water droplets |
|  | 3 | 14 | 2633.4 | 8.744 | 2.57 | Water droplets |
|  | 4 | 30 | 2458.8 | 9.642 | 4.44 | Shrinkage |
|  | 5 | 30 | 2354.4 | 9.842 | 4.65 | Shrinkage |

Additionally, the pH was determined for the three deodorant base composition formulations with the highest PG concentrations at day 30 of the 7 observations. Testing was performed as follows. pH was measured in a 5% solution of the stick formulations and was back calculated to the 100% stick. The formulation containing 69.7 weight % PG:0 weight % Glycerin had a pH of 12.8. The formulation containing 52.3 weight % PG:17.4 weight % Glycerin had a pH of 9.9. The formulation containing 31.4 weight % PG:38.3 weight % Glycerin had a pH of 8.1. Thus, higher percentages of glycerin in the deodorant base compositions correlated with lower pH measurements.

The formulations were also evaluated after 6 months at room temperature. Formulations made without PG showed syneresis (weeping) after only a few days. Mixtures with PG were better in that the stick formulations were reasonably clear and firm. Some evidence of fragrance instability after 6 months was observed especially for stick formulations with higher levels of glycerin.

Deodorancy effectiveness was also tested. The samples were prepared as solutions without the gellant (sodium stearate). Five samples plus one positive control were prepared for testing. PG and glycerin were at the ratios given above. The control consisted of a pH 7.4 buffer. To all samples was added 1 ml of bacterial inoculum of Corynebacterium minutissimum at a concentration of $10^6$/ml, which was then incubated at 37° C. for 2 hours. The samples were then serially diluted in D/E (Dey/Engley) neutralizing broth (−3 to −5 dilutions) and pour plated in triplicate. The plates were incubated for 48 hours and then viewed for bacterial reductions.

The control samples contained approximately $1.74 \times 10^6$ CFU (colony forming units)/ml (7.24 Log) bacteria. The two samples containing higher glycerin concentrations (69.7% and 59.2%) were not significantly different than the control (t-test, alpha=0.05, p=0.14). The sample containing nearly equal amounts of PG and Glycerin, as well as the samples containing higher concentrations of PG completely inhibited the growth of bacteria indicating a >7 Log reduction over 2 hr contact time. The sample with nearly equal amounts of PG and Glycerin along with the high PG samples were significantly better that the control (t-test, alpha=0.05, p=0.015). These samples did not contain any other antibacterial agents or odor control agents.

Anti-Microbial Tests on Deodorants Made from the Deodorant Stick Base Compositions of the Present Invention A commercially available regular Mennen Speed Stick (MSS) deodorant stick, an Ultimate Mennen Speed Stick deodorant stick (containing triclosan as a control) and the PG-free deodorant stick containing glycerin were tested with a Zone Of Inhibition test using 2 cm Webril® (Fiberweb, Gray Court, S.C.) cotton disks on inoculated plates. Also, as controls: water, neat (undiluted) PG and neat glycerin were tested.

Zone of Inhibition Test method: To the disks was added 0.2 g of the stick products or approximately 0.6 g (enough to just saturate the disk) of the neat controls. The disks were then inverted and placed face down on an inoculated agar plate. The agar plates were streaked beforehand (30 minutes) such that a bacterial lawn of Corynebacterium minutissimum at a concentration of $10^6$/ml was created covering the entire plate surface. The plates were then incubated at 37° C. for 48 hrs.

Zones of inhibition were measured in millimeters (mm) from the edge of the disk. A greater zone equals increased bacterial growth inhibition. The results are shown in the Table 2 below.

TABLE 2

| Material | Zone of Inhibition (mm) |
|---|---|
| MSS Ultimate Deodorant | 2.5 |
| MSS regular Deodorant | 1 |
| PG free deodorant | 0.0 |
| 55:45 glycerin/PG deodorant | 1 |
| Water (control) | 0.0 |
| PG neat | 2.5 |
| Glycerin neat | 1 |

The triclosan positive control shows increased antibacterial activity as expected, and the PG-free product produces no inhibition as expected. The deodorant stick containing 45 weight % PG and 55 weight % glycerin produced results similar to the MSS regular deodorant stick demonstrating that reducing the PG level by about half does not reduce efficacy in this test. The glycerin produced a small zone, which is believed may have been due to the occluded surface under and at the fringe of the disk. Glycerin may have occluded air flow to the agar surface resulting in decreased cell viability. This was not seen with the water because it most likely evaporated permitting air exchange.

In one embodiment, compositions according to the invention provide a zone of inhibition of at least 1 mm according to the Zone of Inhibition Test.

Example 2

Comparison of Various PG/Glycerin/Water Deodorant Base Compositions for Criteria Associate with User Appeal Various test samples of deodorants made from various deodorant base compositions of the present invention were tested for hardness (via a penetration test), amount of product applied during use (payout), friction on application (glide), fragrance, base odor, clarity and syneresis (weeping or the contraction of a substance accompanied by the exudation of liquid.).

For the purposes of this experiment, penetration is a measure of product hardness. A cone probe is used on a Texture Technologies TA-XT2 texture analyzer. The force required to move the probe 5 mm into the sample is recorded, using grams as a unit of measure. A 45-degree stainless steel cone is attached to the load cell arm. The arm is lowered by the instrument at a fixed rate—the force required to move the probe the desired distance into the product is recorded. The compositions of the present invention can have a penetration value in an amount of about 700 to about 1100 grams.

Payout is an estimated measure of how much product will be applied in use. The stick is rubbed across a standard substrate using a standard downward force and a specified distance. The amount of product applied to the substrate after 5 cycles (1 cycle being a forward and a backward stroke) is recorded.

Glide is a measure of friction on application. During the payout measurement, the amount of force required to move the stick across the substrate is recorded.

The measurement of payout, friction and glide were tested on a machine specifically designed by the Colgate-Palmolive Corporation for such testing. The machine is the subject of U.S. Patent Application No. 60/976,527, filed Oct. 1, 2007, which was then filed as U.S. patent application Ser. No. 11/971,978, filed Jan. 10, 2008, both of which are herein incorporated by reference in their entirety, and herein referred to as the Test Machine. The compositions of the present invention can achieve a payout of greater than about 0.35 g, 0.4 g, 0.5 g, 0.6 g, 0.7 g, 0.8 g, 0.9 g, or 1 g when tested using the Test Machine.

Fragrance, base odor, clarity and syneresis were evaluated by an experienced chemist, ranked on a scale of 1-5. Syneresis is judged by an experienced chemist on a scale of 1 (Dry surfaces) to 5 (very wet surfaces with liquid seeping out of the package). Color is judged in comparison to a commercial product, with 1 being much lighter, 2 somewhat lighter, 3 equal, 4 somewhat darker and 5 much darker. Clarity is judged on scale of 1=opaque to 5=completely transparent. Fragrance and base odor are evaluated by trained odor evaluators in comparison to a standard (commercially available) product. The standard is arbitrarily set to the middle of the scale (at 3) and intensity is judged in the same way as color (1 being much weaker, 2 somewhat weaker, 3 about the same, 4 somewhat stronger, and 5 much stronger)

The combined data is presented blow in Table 3. Formulas were generated using ranges as follows: PG:10-60%, Glycerin 10-60%, water 10-40%, Sodium Stearate 3-7%.

Sample #12 from the set gave the most desired results (payout>=0.4 grams, syneresis<2, clarity>3). Additional formulas were then prepared. The formulas were: #1, 22% water, 59% PG and 10% glycerin; #2, 28% water, 54% PG and 11% glycerin; and #3, 17.6% water, 30% PG and 45% glycerin. The additional formula (#3) had a ratio of PG/Glycerin/Water that was further improved by the addition of an 80/20 blend of steareth-100 (1.16 weight %) and steareth-2 (0.3 weight %) emulsifier.

TABLE 3

| Sample# | PG | Water | Glycerin | Stearate | Minors (fragrance, color, etc.) | Payout (g) 5 cycles | Payout (g) 10 cycles | Glide 30 mm sec cycle 4-str 1 |
|---|---|---|---|---|---|---|---|---|
| 1 | 30.4 | 16.4 | 47.1 | 4 | Q.S. to 100% | 0.494 | 0.828 | 0.366 |
| 2 | 10 | 20.9 | 60 | 7 | Q.S. to 100% | 0.285 | 0.491 | 0.499 |
| 3 | 10 | 40 | 40.9 | 7 | Q.S. to 100% | 0.235 | 0.463 | 0.309 |
| 4 | 46.9 | 16.4 | 30.6 | 4 | Q.S. to 100% | 0.583 | 0.983 | 0.325 |
| 5 | 24 | 20.8 | 47.1 | 6 | Q.S. to 100% | 0.322 | 0.543 | 0.375 |
| 6 | 60 | 16.6 | 14.3 | 7 | Q.S. to 100% | 0.505 | 0.789 | 0.393 |
| 7 | 40.1 | 40 | 10.8 | 7 | Q.S. to 100% | 0.217 | 0.378 | 0.323 |
| 8 | 27 | 7.9 | 60 | 3 | Q.S. to 100% | 0.638 | 1.003 | 0.455 |
| 9 | 10 | 40 | 44.9 | 3 | Q.S. to 100% | 0.628 | 1.036 | 0.224 |
| 10 | 46.9 | 22.5 | 22.5 | 6 | Q.S. to 100% | 0.450 | 0.752 | 0.364 |
| 11 | 60 | 24.1 | 10.8 | 3 | Q.S. to 100% | 0.754 | 1.221 | 0.253 |
| 12 | 46.9 | 24.5 | 22.5 | 4 | Q.S. to 100% | 0.494 | 0.823 | 0.293 |
| 13 | 39 | 32.5 | 22.5 | 4 | Q.S. to 100% | 0.368 | 0.606 | 0.268 |
| 14 | 60 | 20.1 | 10.8 | 7 | Q.S. to 100% | 0.467 | 0.766 | 0.384 |
| 15 | 21.9 | 32.5 | 37.5 | 6 | Q.S. to 100% | 0.310 | 0.500 | 0.359 |
| 16 | 33.8 | 24.9 | 34.2 | 5 | Q.S. to 100% | 0.391 | 0.614 | 0.339 |
| 17 | 21.9 | 32.5 | 39.5 | 4 | Q.S. to 100% | 0.445 | 0.723 | 0.285 |
| 18 | 21.9 | 22.9 | 47.1 | 6 | Q.S. to 100% | 0.379 | 0.623 | 0.396 |
| 19 | 37 | 32.5 | 24.5 | 6 | Q.S. to 100% | 0.269 | 0.464 | 0.304 |
| 20 | 60 | 7.9 | 27 | 3 | Q.S. to 100% | 1.015 | 1.356 | 0.268 |
| 21 | 14.3 | 16.6 | 60 | 7 | Q.S. to 100% | 0.302 | 0.555 | 0.408 |
| 22 | 44.1 | 40 | 10.8 | 3 | Q.S. to 100% | 0.516 | 0.800 | 0.231 |
| 23 | 46.9 | 20.8 | 24.2 | 6 | Q.S. to 100% | 0.425 | 0.693 | 0.321 |
| 24 | 21.9 | 24.9 | 47.1 | 4 | Q.S. to 100% | 0.414 | 0.704 | 0.325 |
| 25 | 10 | 24.9 | 60 | 3 | Q.S. to 100% | 0.759 | 1.052 | 0.289 |

TABLE 3-continued

| Sample# | Glide 30 mm sec cycle 4-str 2 | Penetration force (g/5 mm) | Fragrance | Base Odor | Clarity | Color | Wetness Syneresis |
|---|---|---|---|---|---|---|---|
| 1 | 0.600 | 911 | 3.2 | 2.8 | 5 | 5 | 4 |
| 2 | 0.579 | 1364 | 3.4 | 3 | 4 | 4 | 2.5 |
| 3 | 0.543 | 909 | 3.2 | 3.4 | 1 | 1 | 1 |
| 4 | 0.554 | 897 | 4.1 | 1.4 | 5 | 4 | 3.5 |
| 5 | 0.619 | 1379 | 3.2 | 3.1 | 4 | 5 | 1.5 |
| 6 | 0.627 | 962 | 4.2 | 1 | 2 | 4 | 1.5 |
| 7 | 0.559 | 1165 | 3.4 | 2 | 4 | 2 | 1 |
| 8 | 0.690 | 865 | 2.6 | 3 | 5 | 5 | 5 |
| 9 | 0.443 | 368 | 2.6 | 3 | 1 | 1 | 5 |
| 10 | 0.595 | 1052 | 4.2 | 1.55 | 2 | 4 | 2 |
| 11 | 0.483 | 527 | 4.4 | 1.2 | 5 | 4 | 3 |
| 12 | 0.514 | 868 | 4.6 | 1.2 | 5 | 4 | 2 |
| 13 | 0.496 | 954 | 4.4 | 1.6 | 4 | 4 | 2 |
| 14 | 0.614 | 1017 | 4 | 1.1 | 4 | 3.5 | 1.5 |
| 15 | 0.601 | 1215 | 4.8 | 2.9 | 3 | 3.5 | 2 |
| 16 | 0.568 | 1056 | 4.4 | 1.4 | 4 | 4.5 | 2 |
| 17 | 0.506 | 719 | 3 | 2.4 | 3 | 4 | 3.5 |
| 18 | 0.635 | 1041 | 2.7 | 2.2 | 2 | 4 | 5 |
| 19 | 0.530 | 1312 | 3.4 | 1.5 | 2 | 4 | 1 |
| 20 | 0.484 | 382 | 4.8 | 1.2 | 3 | 4.5 | 5 |
| 21 | 0.656 | 1462 | 2.8 | 2.8 | 4 | 5 | 3 |
| 22 | 0.450 | 576 | 4.2 | 2.8 | 2 | 3 | 4 |
| 23 | 0.556 | 1045 | 4 | 1.4 | 5 | 4.5 | 2 |
| 24 | 0.548 | 978 | 3.4 | 2.4 | 4 | 5 | 3 |
| 25 | 0.506 | 306 | 2.9 | 3.8 | 2 | 3.5 | 5 |

Example 3

Comparison of Irritability Between Propylene Glycol-Based Deodorant Compositions and PG/Glycerin/Water-Based Deodorant Compositions Experiments were performed on EpiDerm™ (MatTek Corporation, Ashland, Mass.) reconstructed human skin model products designed specifically for assessing irritability from substances applied to human skin. Protocols used were those recommended by the manufacturer and reviewed in: Kandarova, et al., "Assessment of the Skin Irritation Potential of Chemicals by Using the SkinEthic Reconstructed Human Epidermal Model and the Common Skin Irritation Protocol Evaluated in the ECVAM Skin Irritation Validity Study," Altern. Lab. Animals (ATLA), 34(4):393-406, 2006.

The protocol was based on ET-50 data. That is, the time at which 50% of the skin cells were estimated to remain viable after exposure to the test material. Results were categorized as follows based on ET-50 as given in Table 4.

TABLE 4

| ET-50 (hours) | Expected in vivo irritancy |
|---|---|
| <0.5 | Strong/severe, possibly corrosive |
| 0.5-4 | Moderate |
| 4-12 | Moderate to mild |
| 12-24 | Very mild |
| 24 | Non-irritating |

The results showed that the deodorant composition based on the deodorant base compositions of the present invention were characterized as "very mild" whereas the deodorant composition based on the deodorant base composition of a 66% propylene glycol prior art formulation was characterized as moderate to mild. These results clearly show a reduced level of irritability with the deodorant base compositions of the present invention as compared to a commonly used prior art formulation. The data is presented in Table 5. Percents indicated % w/w of the total deodorant composition and do not add up to 100%. The remainder of the formulation includes 7% w/w sodium stearate as a gellant as well as small percentages of deodorancy agents, fragrance and other minor ingredients.

TABLE 5

| Test article | ET-50 | Determined in vivo irritancy |
|---|---|---|
| Deo stick (45% PG, 18% glycerin, 29% water) | >18.0 | Very mild |
| Deo stick (45% PG, 18% glycerin, 29% water) | >18.0 | Very mild |
| Deo. stick (47% PG, 22% glycerin, 18% water) | >18.0* | Very Mild |
| Deo stick (66% PG, no glycerin, 26% water) | 8.9 | Moderate to mild |

*Results predicted based on investigator feedback.

APPENDIX

The description below is the text from U.S. application Ser. No. 11/971,978, filed on 10 Jan. 2008. This text is being included as a description of how to run the payout, glide, and flakeoff tests on the described Test Machine. All terms and definitions in this Appendix Section only apply to the Test Machine.

In an embodiment of the present invention, a system for measuring any or all of payout, static friction and kinetic friction is disclosed. The system includes at least one substrate positioned on an XYZ translational substrate bed. The system includes a sample holder for supporting a sample, wherein the sample holder and the sample are positioned perpendicular to the XYZ translational substrate bed. The system further includes a force device placing a predetermined weight onto the sample holder; the predetermined weight determines a contact force placed by the sample onto the substrate. The system also includes frictionless bearing table connected to the sample holder and a stationary frictionless bearing table positioned parallel to the XYZ translational substrate bed. The sample holder and the stationary frictionless bearing table are connected to a friction sensor. The system also includes a balance for obtaining a first substrate weight before movement of the XYZ translational substrate bed and a second substrate weight after movement of the XYZ translational substrate bed.

The system further includes a controller operably coupled to the moving substrate bed and the friction sensor and configured to execute a machine readable program code containing executable instructions.

In an embodiment of the present invention, a method for measuring payout is disclosed. The method comprises positioning a substrate of pre-known weight on an XYZ translational substrate bed; supporting a sample in a sample holder, wherein the sample is perpendicular to the XYZ translational substrate bed; placing a predetermined weight onto the sample holder so that the sample and substrate form a contact point; first moving the XYZ translational substrate bed at a first sweep speed in a first direction relative to the sample; second moving the XYZ translational substrate bed at a second sweep speed in a second direction relative to the sample; conducting the first moving and the second moving for a predetermined number of cycle(s); obtaining a second substrate weight of the substrate after the predetermined number of cycles; and determining a payout value based on the first substrate weight and the second substrate weight.

In an embodiment of the present invention, a method for measuring one or more of static friction and kinetic friction is provided. The method comprises: positioning a substrate of pre-known weight on an XYZ translational substrate bed; supporting a sample in a sample holder, wherein the sample is perpendicular to the XYZ translational substrate bed; placing a predetermined weight onto the sample holder so that the sample and substrate form a contact point; first moving the XYZ translational substrate bed at a first sweep speed in a first direction relative to the sample; second moving the XYZ translational substrate bed at a second sweep speed in a second direction relative to the sample; conducting the first moving and the second moving for a predetermined number of cycle(s); during the first moving step and the second moving step, measuring one or more friction values at the contact point; analyzing one or more friction values generated at the sample contact point during the first moving step and the second moving step; and determining one or more of a static friction value and a kinetic friction value based on the one or more friction values.

In an embodiment of the present invention, a method for measuring flakeoff is provided. The method comprises: providing a wool sample of a predetermined size; applying an initial weight of a material to the wool sample; attaching a first end of the wool to a stationary holder and a second end to a movable substrate bed; a stretching step comprising moving the movable substrate bed a predetermined distance and returning and then moving it to an opposite direction for the same predetermined distance and returning for 1 stretch; repeating the stretch step for a predetermined number of stretches; measuring the weight of the wool sample and material after the predetermined number of stretches; determining a weight loss of material from the wool sample as measured by an amount of material lost from the sample divided by the initial weight of material after the predetermined number of stretches.

In each of the above methods, the methods are conducted on the above described system.

BRIEF DESCRIPTION OF DRAWINGS

Reference will now be made in detail to embodiments of the present disclosure, examples of which are illustrated in the accompanying drawings. Wherever possible, the same reference numbers will be used throughout the drawings to refer to the same or like parts.

Figure 1:
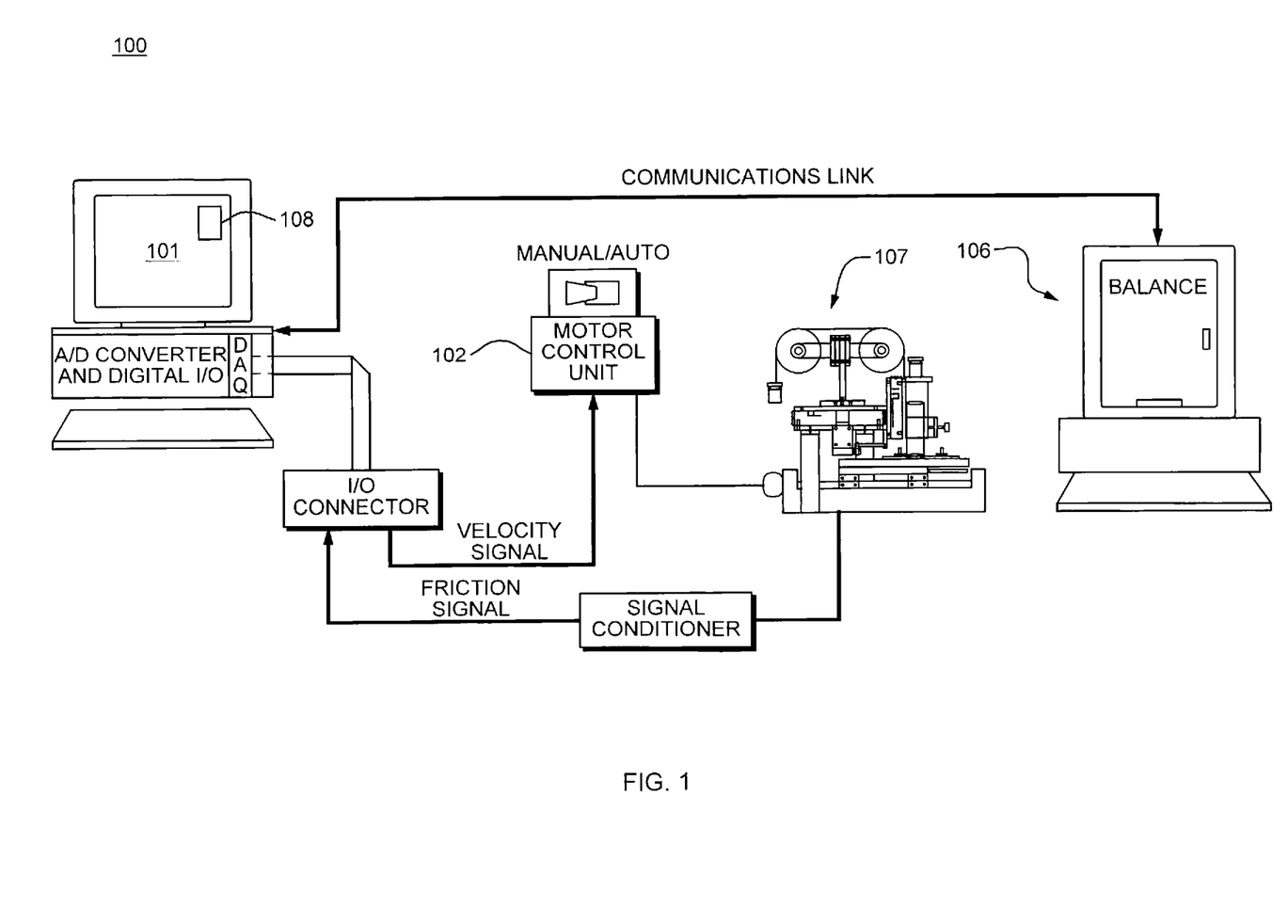
FIG. 1 illustrates an exemplary system to measure payout, static friction, kinetic friction, and combinations thereof.

Appendix FIG. 1 illustrates an exemplary system to measure payout, static friction, kinetic friction, and combinations thereof.

Figure 2:
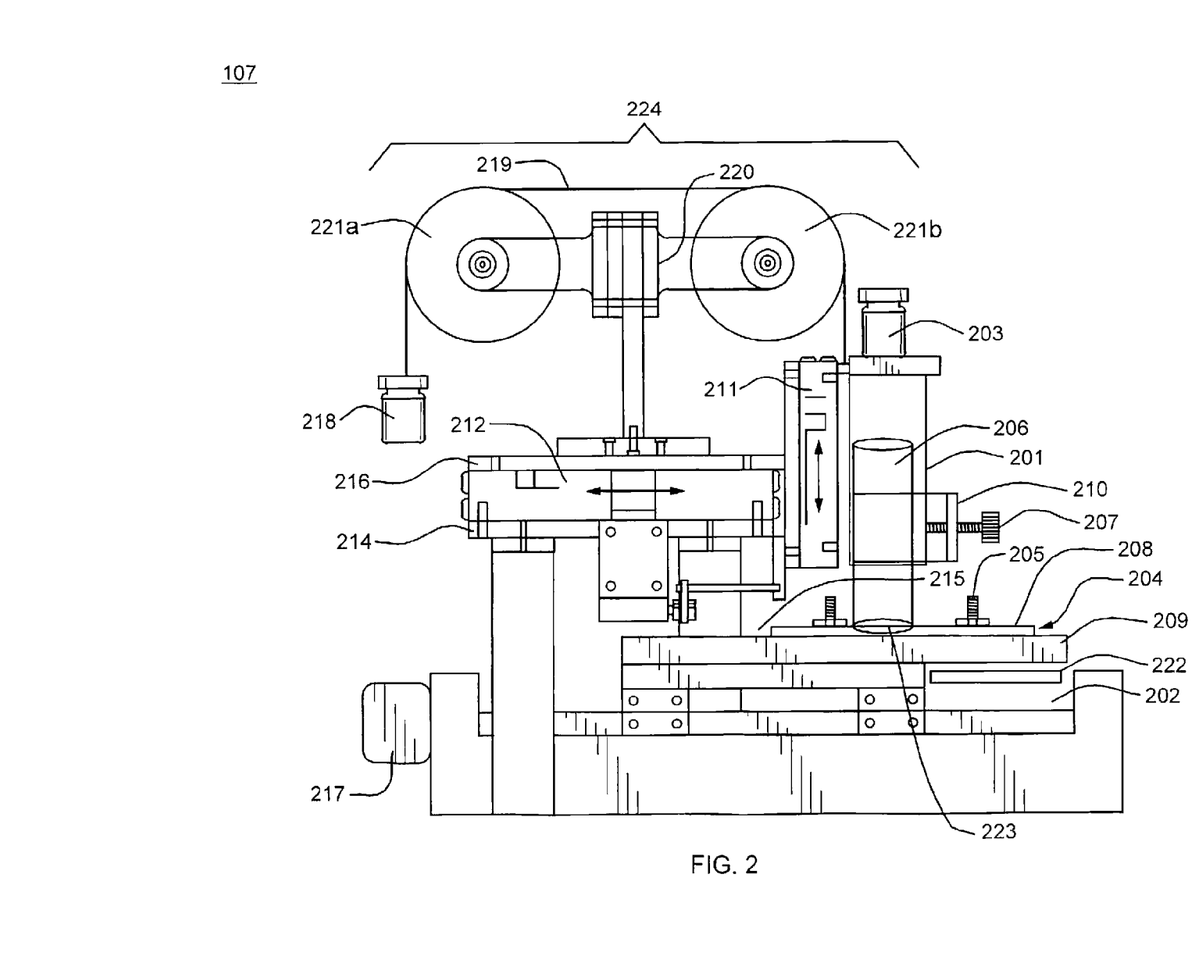
FIG. 2 illustrates an exemplary device to measure payout, static friction, kinetic friction, and combinations thereof.

Appendix FIG. 2 illustrates an exemplary device to measure payout, static friction, kinetic friction, and combinations thereof.

Figure 3:
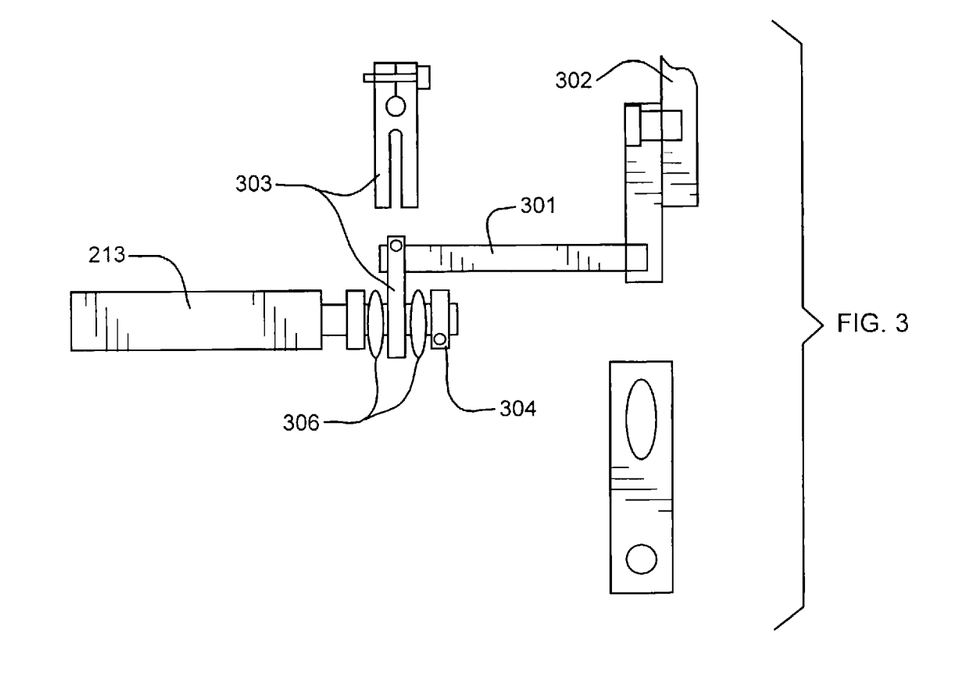
FIG. 3 illustrates an exemplary friction sensor.

Appendix FIG. 3 illustrates an exemplary friction sensor.

Figure 4:
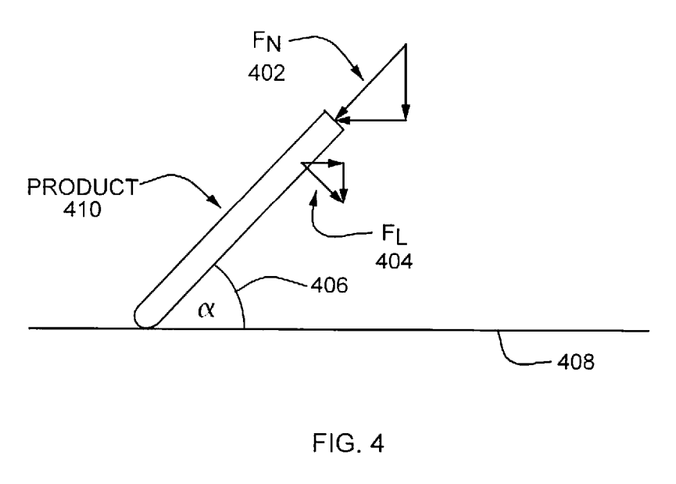
FIG. 4 illustrates a model for determining the friction coefficient.

Appendix FIG. 4 illustrates a model for determining the friction coefficient.

Figure 5:
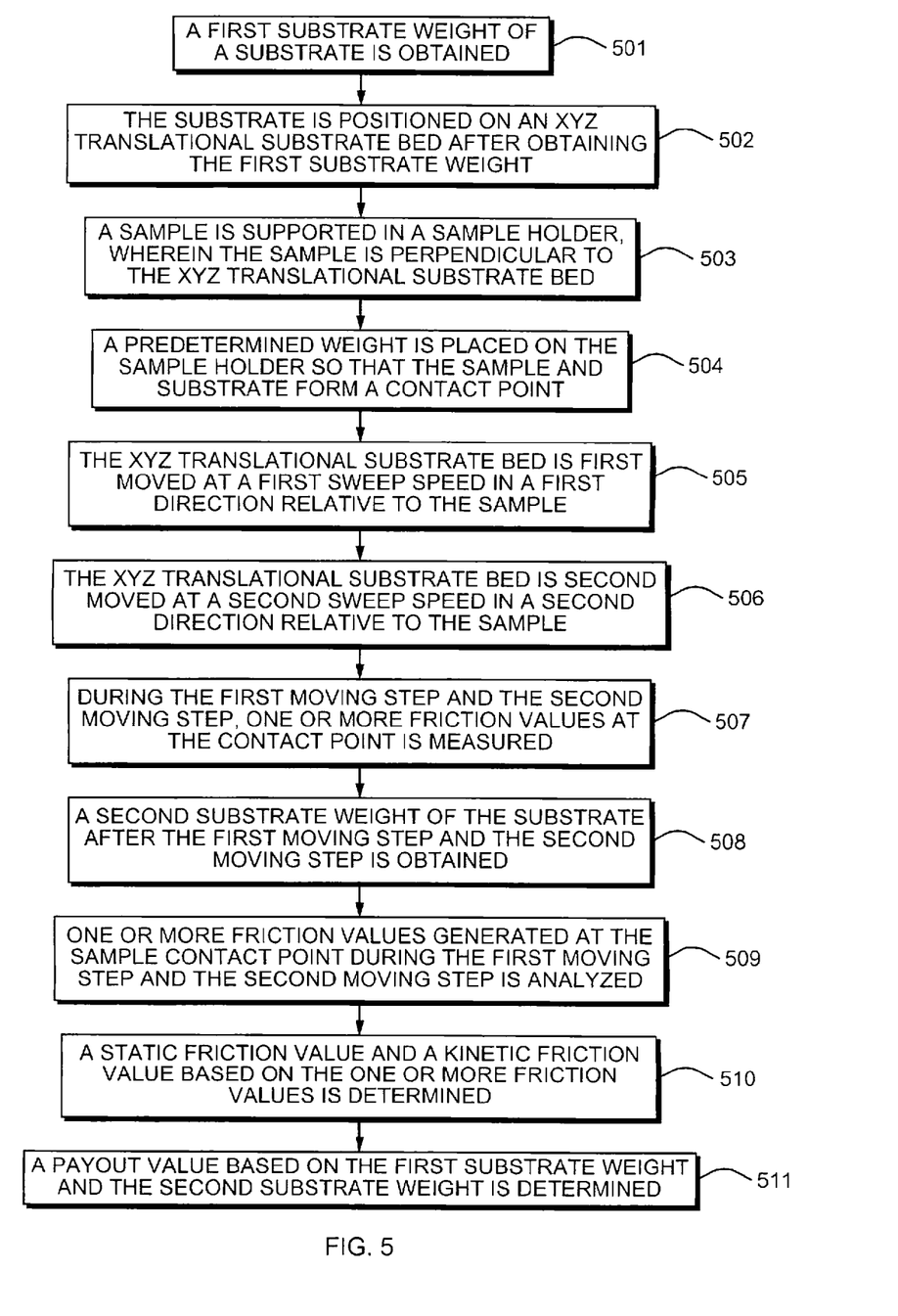
FIG. 5 illustrates an exemplary method using the systems described herein.

Appendix FIG. 5 illustrates an exemplary method using the systems described herein.

DETAILED DESCRIPTION OF THE INVENTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a reference, the present disclosure controls.

The present invention provides for systems and methods for measuring payout, static friction, kinetic friction or combinations thereof. Appendix FIG. 1 illustrates an exemplary system 100 including a payout friction tester device 107, a balance 106, and a controller 101 having a machine readable program code 108 containing executable instructions. The device 107 for measuring payout, static friction, kinetic friction or combinations thereof can be operably linked to the controller 101 through a motor control unit 102. The components of the exemplary system 100 illustrated in Appendix FIG. 1 are described further below.

Appendix FIG. 2 illustrates an exemplary payout friction device 107. Device 107, of system 100, includes: at least one substrate 204 positioned on an XYZ translational substrate bed 209; a sample holder 201; a force device 224; a frictionless bearing table 211; a stationary frictionless bearing table 212; and a friction sensor 213. Sample holder 201 supports sample 206 so that the sample 206 can be positioned perpendicular to the XYZ translational substrate bed 209 or so that the sample 206 contacts the substrate 204 perpendicularly. The sample holder 201 can also support the sample 206 such that the sample 206 contacts the substrate 204 at an angle that is less than 90°.

Sample 206 can be any sample that can be analyzed for payout, static friction, kinetic friction or combinations thereof. Examples of samples include but are not limited to deodorants (e.g. a deodorant stick), antiperspirants, or combinations thereof. The sample 206 can be secured to the sample holder 201 using a screw 207, such as a knurled thumbscrew, or other means for attachments, such as a clip or other means that can secure the sample 206 and assist in orienting its alignment. The sample clamp 210 can accept deodorant stick canisters 206 or other types of sample containers of various sizes and configurations.

Substrate 204 may include materials such as copier grade paper, sandpaper (in differing grades of abrasion) or cloth may be used. In some embodiments, it is convenient to cut the substrate beforehand in bulk, for example, into approximately 13×25 centimeter strips so that single strips can be clamped in place before testing.

Referring again to Appendix FIG. 2, the XYZ translational substrate bed 209 functions to move the XYZ translational substrate bed at a first sweep speed in a first direction and at a second sweep speed in a second direction relative to the sample 206. The XYZ translational substrate bed 209 is operably coupled to a motorized screw table 202. The motorized screw table 202 can be driven by an electronic drive unit 217. The electronic drive unit 217 can operate in an automated mode or a manual mode. In the automatic mode, the electronic drive unit 217 can include a pulse width modulation speed control so to achieve precise speed control down to a zero velocity high torque condition. The motor 103 can be remotely driven by a velocity signal furnished by the controller 101, for example by the controller's analog output channel. This allows precise control over the sweep rate and distance. In the manual mode, an operator manipulates the XYZ translational substrate bed 209 using controls of the electronic drive unit 102. An example of an electronic drive unit 217 is, but not limited to, a Motamatic Drive Unit.

In one embodiment, the XYZ translational substrate bed 209 also includes a heater 222. In some embodiments, the heater 222 is capable of heating the substrate 204 to a temperature of about 26.7° C. to about 43.3° C. (about 80° F. to about 110° F.), about 32.2° C. to about 43.3° C. (about 90° F. to about 110° F.), about 32.2° C. to about 37.8° C. (about 90° F. to about 100° F.), about 35° C. to about 37.8° C. (about 95° F. to about 100° F.), about 36.7° C. to about 37.8° C. (about 98° F. to about 100° F.), 36.7° C. to about 37.2° C. (about 98° F. to about 99° F.), or about 37° C. (about 98.6° F.).

Frictionless bearing table 211 is connected to the sample holder 201 permitting "frictionless" movement of the sample 206 supported by the sample holder 201. In some embodiments, the frictionless bearing table 211 is positioned perpendicular to the XYZ translational substrate bed 209. In other embodiments, the frictionless bearing table 211 is positioned vertically. The frictionless bearing table 211 functions to maintain an axis of pressure with testing and permits up and down movement of the sample holder 201. The weight of the sample holder 201 can be counter balanced to zero force through counterweight 218 via the pulley tower 220 and cable 219. Additional weight(s) 203 are placed on top of the sample holder 201 to define the magnitude of contact force (that which presses the sample against the surface).

A stationary frictionless bearing table 212 is positioned parallel to the XYZ translational substrate bed 209. In some embodiments, the stationary frictionless bearing table 212 is a horizontal frictionless bearing table. In other embodiments, the stationary frictionless bearing table 212 is positioned on internal rails supported by a plurality of ball bearings. The stationary frictionless bearing table floor 214 is part of the base 216 for device 107 and does not move permitting the measurement of force with respect to a solid reference.

Friction sensor 213 is operably connected to the sample holder 201 and the stationary frictionless bearing table 209. In one embodiment, friction sensor 213 can be mounted above the XYZ translational bed 209 on a bracket secured to the stationary frictionless bearing table floor 214. Lateral friction is transmitted to the friction sensor 213 through a linkage 215 coupling arrangement. This linkage 215 can be oriented as close as practical to the plane of actual friction. Measuring friction at the sample contact point 223 requires that other friction points in the machine be eliminated or at least minimized as much as possible. To accomplish this, the stationary frictionless bearing table 212 supports the upper assembly completely. All of the assembly components can be bound together on a supporting structure 216 (shown as a sideways T in black). This "rides" as one piece on the stationary frictionless bearing table 212.

The friction sensor 213 can be any sensor that can be used to detect and determine friction. Transferring surface friction to the sensing element can be done by a mechanical linkage from the sample holder 201 to the friction sensor 213. Referring to Appendix FIG. 3, the friction sensor 213 is operably coupled to a linkage 215 including a transmitter bar 301 and a linkage fork 303. Transmitter bar 301 connects registered force at the sample contact point 223 (Appendix FIG. 2) from the sample carriage mount 302 to the linkage fork 303. The linkage fork 303 can be positioned between a pair of O-ring dampeners 306 and the pair of O-ring dampeners can be positioned between a pair of element stops 304. The linkage fork 303 is suspended between two element stops 304 attached to the friction sensor probe 305. When the linkage fork 303 pushes against a stop its force content is transferred to the friction sensor 213. Physical contact at the stops is intentionally dampened by rubber "O" rings 306 which assist in smoothing out the elastic ringing that results from abrupt changes in force direction Referring again to Appendix FIG. 2, device 107 can include a force device 224 including a predetermined weight 203, a counter weight 218, a cord 219, a pulley tower 220, and two pulleys 221a and 221b. Force device 224 functions to place a predetermined weight 203 onto sample holder 201 where the predetermined weight 203 determines a contact force placed by the sample 206 onto the substrate 204. The predetermined weight 203 and the counter weight 218 can be connected by the cord 219. In some embodiments, the stationary frictionless bearing table 212 supports force device 224.

Referring to both Appendix FIG. 1 and Appendix FIG. 2, system 100 may also include a controller 101. For monitoring and controlling the desired variables. Any type of controller can be used to operate the system. Installed in the controller is a multi-functional A/D converter card (DAQ) providing the necessary interface to the system to the various components. Controller 101 is operably coupled to the XYZ translational substrate bed 209, the balance 106, and the friction sensor 217 and configured to execute the machine readable program code 108. Controller 101 is configured to execute machine readable program code 108 to perform various functions. In some embodiments, the functions include, but are not limited to configuring the balance 106 to obtain the first substrate weight before movement of the XYZ translational substrate bed 209 and the second substrate weight after movement of the XYZ translational substrate bed 209. Controller 101 also configures the XYZ translational substrate bed 209 to move the XYZ translational substrate bed 209 at a first sweep speed in a first direction and at a second sweep speed in a second direction relative to the sample 206. Controller 101 also analyzes one or more friction values, measured by the friction sensor, generated at the sample contact point 223 located between the sample 206 and the substrate 204 during movement of the XYZ translational substrate bed 209. Controller 101 is further configured to perform the determine a static friction value and a kinetic friction value based on the one or more friction values or determine a payout value based on the first substrate weight and the second substrate weight.

The system of the present invention can also be configured to execute machine readable code containing executable program instructions to perform a variety of functions. In some embodiments, the system is configured to perform methods for measuring one or more of the following: payout, static friction and kinetic friction. One embodiment for measuring one or more of the following: payout, static friction and kinetic friction is illustrated in Appendix FIG. 5. In step 501, a first substrate weight of a substrate is obtained. In one embodiment, a fresh piece of substrate 204 is placed into the balance 106 to be weighed. A continuous reading from the balance 106 is displayed in the window as the balance 106 is loaded. Once a stable reading is noted it can be "acquired" by pushing an on screen button labeled "Get weight". The substrate 204 is then removed from the balance 106 and secured to the XYZ translational bed 209 with clamping plates 208 on the longitudinal sides.

In step 502 the substrate is positioned on an XYZ translational substrate bed after obtaining the first substrate weight. In step 503 a sample is supported in a sample holder, wherein the sample is perpendicular to the XYZ translational substrate bed. In Step 504 a predetermined weight is placed onto the sample holder so that the sample and substrate form a contact point.

In step 505 the XYZ translational substrate bed 209 is first moved at a first sweep speed in a first direction relative to the sample. In step 506 the XYZ translational substrate bed is second moved at a second sweep speed in a second direction relative to the sample. In one embodiment, controller 101 begins the sweeping process when permission is given by an operator. In another embodiment, controller 100 begins the sweeping process based on an automated process where permission is not needed but instead the process begins when the sample 206 and the substrate 204 are secured. The sweeping steps 505 and 506, are performed by a motorized screw table that is driven by an electronic drive unit. The electronic drive unit can have a pulse width modulation speed control. In some embodiments, the first moving step and the second moving step are repeated a predetermined number of times. In some embodiments, the first moving step and the second moving step are performed 1-50, 1-40, 1-30, 1-20, 1-10, 5-10, 5-15, 5, or 10 times.

The distance moved in the first direction or the second direction by the XYZ translational substrate bed 209, during the sweep steps 505 and 506 can be varied. In some embodiments, the distance of the first direction or the second direction is about 5 to about 50 cm, about 5 to about 40 cm, about 5 to about 30 cm, about 5 to about 20 cm, about 5 to about 10 cm. In some embodiments, distance of the first direction or the second direction is about 5, about 10, about 15, about 20, about 25, about 30, about 35, about 40, or about 50 cm.

In step 507 during the first moving step and the second moving step, one or more friction values at the contact point is measured. In some embodiments, lateral friction can be measured directly as the XYZ translational substrate bed 209 sweeps in the first and second directions. In one embodiment, each response from the friction sensor 213 can be displayed in real time at controller 101, as the sweeping continues.

In step 508 a second substrate weight of the substrate after the first moving step and the second moving step is obtained. When the requested number of sweep steps has occurred the computer can re-display the "Get weight" window. The impregnated material, i.e. substrate 204, can be removed from the lower bed and placed back into the balance 106 to be post-weighed. Payout is determined from the change in weight of the substrate 204.

In step 509 one or more friction values generated at the sample contact point during the first moving step and the second moving step is analyzed. In step 510 a static friction value and a kinetic friction value based on the one or more friction values are determined. In some embodiments the friction values are determined using the formula described herein. In step 511 a payout value based on the first substrate weight and the second substrate weight is determined.

The present invention also provides for determining friction coefficients as the substrate and sample pass against one another. Using the systems described herein the sample moves or glides across the substrate in a pattern that involves acceleration and de-acceleration unlike the previous assumption that the motion occurs with uniform speed. Therefore, the following model based on Newton's second law was employed to calculate the coefficient of friction between the sample and the substrate. Appendix FIG. 4 illustrates a model configuration of the substrate and sample passing against one another where $F_N$ is the normal force applied to the skin 408, $F_L$ is the net lateral force across the skin 408, $\alpha$ is the angle between the product 410 and the skin 408 at any given time. Based on the configuration displayed in Appendix FIG. 4, the friction coefficient at any given time can be express as following:

Driving force=$F_L \sin(\alpha) - F_N \cos(\alpha)$; Friction Force=$\mu^*[F_L \cos(\alpha) + F_N \sin(\alpha)]$; Newton's second law: $F_L \sin(\alpha) - F_N \cos(\alpha) - \mu^*[F_L \cos(\alpha) + F_N \sin(\alpha)] = m^*a$; $\mu = \{F_L \sin(\alpha) - F_N \cos(\alpha) - m^*a\} / [F_L \cos(\alpha) + F_N \sin(\alpha)]$; where $m^*a$ is the inertia of the (carriage+sample) times acceleration($a$).

The device 107 can also be used to measure flakeoff. Flakeoff is a measure of weight loss of material from a sample that has been stretched. It is a measure of how well a material (such as an antiperspirant/deodorant composition) will remain on a substrate. In one embodiment, a predetermined amount of material (for example, 0.65±0.03 g) to be tested is applied onto a piece of wool (Style #530 from Testfabrics, Inc.) of a predetermined size (for example, 7.6 cm×15.2 cm (3 in.×6 in.)). The wool is stretched a predetermined distance (for example 6 cm) and returned and then stretched to the opposite direction for the same predetermined distance and returned as one stretch. The weight of the wool and material is measured after a predetermined number of stretches (for example 50, 150, and/or 450 stretches). The percent weight loss of the material from the wool is recorded as a measure of flake-off. In one embodiment, the results from four samples can be averaged to give an averaged result. In device 107, one end of the wool is attached to a stationary holder, which is attached to the frictionless bearing table 211 as replacement of sample holder 201, and the other end of the wool is attached to substrate bed 209; oriented across the 15.2 cm length. The wool is thus perpendicular to the substrate bed 209. Substrate bed 209 is then moved to stretch the wool.

EXAMPLES

Example 1: Payout/Glide on Sample

Payout on a sample is measured using the system described herein. The system holds the deodorant stick flush to the substrate and moves the stick with a set speed over a distance of 100 mm with 500 g of force. The payout program measures the amount of the product applied to a cotton substrate after 10 strokes, whereas the glide program measures the friction to move the stick across the substrate during one stroke. Immediately prior to payout analysis, three sticks of each experimental stick are cut flat and then the stick surface was is further flattened or conditioned on the instrument using a speed of 30 mm/sec for 20 cycles. In order to determine the payout, the cotton substrate is tared on a balanced and then clamped down on the substrate bed. The stick is passed over the substrate 10 times at a speed of 20 mm/sec, and then the substrate is removed and returned to the balance to obtain the weight of the product on the substrate. The payout is measured three times on a stick and the average of the three results is calculated. The friction coefficient for the first and tenth strokes is recorded.

A system for measuring one or more of the following: payout, static friction and kinetic friction comprising:
  at least one substrate positioned on an XYZ translational substrate bed;
  a sample holder for supporting a sample, wherein the sample holder and the sample are positioned perpendicular to the XYZ translational substrate bed;
  a force device placing a predetermined weight onto the sample holder, the predetermined weight determining a contact force placed by the sample onto the substrate;
  a frictionless bearing table connected to the sample holder;
  a stationary frictionless bearing table positioned parallel to the XYZ translational substrate bed;
  a friction sensor connected to the sample holder and the stationary frictionless bearing table;
  a balance for obtaining a first substrate weight before movement of the XYZ translational substrate bed and a second substrate weight after movement of the XYZ translational substrate bed;
  a machine readable program code containing executable instructions; and
  a controller operably coupled to the moving substrate bed, the balance, and the friction sensor and configured to execute the machine readable program code so to perform the following:
    configure the balance to obtain the first substrate weight and the second substrate weight;
    configure the XYZ translational substrate bed to move the XYZ translational substrate bed at a first sweep speed in a first direction and at a second sweep speed in a second direction relative to the sample; and
    analyze one or more friction values, measured by the friction sensor, generated at the sample contact point located between the sample and the substrate during movement of the XYZ translational substrate bed.

The system of [Appendix 0040], wherein the sample comprises an antiperspirant or deodorant stick.

The system of [Appendix 0040], wherein the XYZ translational substrate bed is operably coupled to a motorized screw table.

The system of [Appendix 0042], wherein the motorized screw table is driven by an electronic drive unit.

The system of [Appendix 0043], wherein the electronic drive unit has pulse width modulation speed control.

The system of [Appendix 0040], wherein the friction sensor is operably coupled to a linkage comprising a transmitter bar and a linkage fork.

The system of [Appendix 0045], wherein the transmitter bar is connected to the sample holder and the linkage fork, and wherein the linkage fork is further coupled to the friction sensor.

The system of [Appendix 0046], wherein the linkage fork is positioned between a pair of O-ring dampeners and the pair of O-ring dampeners are positioned between a pair of element stops.

The system of [Appendix 0040], wherein the force device comprises the predetermined weight, a counter weight, a cord, a pulley tower and two pulleys, wherein the predetermined weight and the counter weight are connected by the cord.

The system of [Appendix 0040], wherein stationary frictionless bearing table is positioned on internal rails supported by a plurality of ball bearings.

The system of [Appendix 0040], wherein the controller is further configured to perform the following:
  based on the one or more friction values, determine a static friction value and a kinetic friction value; and
  based on the first substrate weight and the second substrate weight, determine a payout value.

The system of [Appendix 0040], wherein the sample holder supports the sample in a vertical position.

The system of [Appendix 0040], wherein the force device comprises a vertical force device.

The system of [Appendix 0040], wherein the stationary frictionless bearing table comprises a horizontal frictionless bearing table.

The system of [Appendix 0040], wherein the XYZ translational substrate bed includes a heater.

A method for measuring payout comprising:
  positioning a substrate of pre-known weight on an XYZ translational substrate bed;
  supporting a sample in a sample holder, wherein the sample is perpendicular to the XYZ translational substrate bed;
  placing a predetermined weight onto the sample holder so that the sample and substrate form a contact point;
  first moving the XYZ translational substrate bed at a first sweep speed in a first direction relative to the sample;
  second moving the XYZ translational substrate bed at a second sweep speed in a second direction relative to the sample;
  conducting the first moving and the second moving for a predetermined number of cycle(s);
  obtaining a second substrate weight of the substrate after the predetermined number of cycles; and
  determining a payout value based on the first substrate weight and the second substrate weight.

The method of [Appendix 0055], wherein the first sweep speed and the second sweep speed is 20 mm/s, the predetermined number of cycles is 10, a total distance traveled in one cycle is 100 mm, and the sample is applied to the substrate at a 500 g force.

The method of [Appendix 0055] further comprising preconditioning the sample comprising conducting the method in [Appendix 0055] up to the conducting step for 20 cycles at a first sweep speed and second sweep speed of 30 mm/s on a substrate that is then discarded.

The method of [Appendix 0055], wherein the XYZ translational substrate bed is heated to a temperature of 37° C.

The method of [Appendix 0055], wherein the sample comprises an antiperspirant or deodorant stick.

A method for measuring one or more of static friction and kinetic friction comprising:
  positioning a substrate of pre-known weight on an XYZ translational substrate bed;
  supporting a sample in a sample holder, wherein the sample is perpendicular to the XYZ translational substrate bed;

placing a predetermined weight onto the sample holder so that the sample and substrate form a contact point;
first moving the XYZ translational substrate bed at a first sweep speed in a first direction relative to the sample;
second moving the XYZ translational substrate bed at a second sweep speed in a second direction relative to the sample;
conducting the first moving and the second moving for a predetermined number of cycle(s);
during the first moving step and the second moving step, measuring one or more friction values at the contact point;
analyzing one or more friction values generated at the sample contact point during the first moving step and the second moving step; and
determining one or more of a static friction value and a kinetic friction value based on the one or more friction values.

The method of [Appendix 0060] further comprising preconditioning the sample comprising conducting the method in [Appendix 0060] up to the conducting step for 20 cycles at a first sweep speed and second sweep speed of 30 mm/s on a substrate that is then discarded.

The method of [Appendix 0060], wherein the XYZ translational substrate bed is heated to a temperature of 37° C.

The method of [Appendix 0060], wherein the sample comprises an antiperspirant or deodorant stick.

A method of measuring flakeoff of a material comprising:
providing a wool sample of a predetermined size;
applying an initial weight of a material to the wool sample;
attaching a first end of the wool to a stationary holder and a second end to a movable substrate bed;
a stretching step comprising moving the movable substrate bed a predetermined distance and returning and then moving it to an opposite direction for the same predetermined distance and returning for 1 stretch;
repeating the stretch step for a predetermined number of stretches; measuring the weight of the wool sample and material after the predetermined number of stretches;
determining a weight loss of material from the wool sample as measured by an amount of material lost from the sample divided by the initial weight of material after the predetermined number of stretches.

The method of [Appendix 0064], wherein the wool sample measures 7.6 cm×15.2 cm and the initial weight of material is 0.65±0.03 g.

The method of [Appendix 0064], wherein the predetermined distance is 6 cm.

The method of [Appendix 0064], wherein the predetermined number of stretches is 50 and optionally one or more of 150 and 450.

We claim:

1. A stick-type deodorant base composition comprising:
a) an alcohol consisting of propylene glycol and glycerin;
b) water; and
c) a thickening agent;
in an amount so that the composition forms a deodorant stick wherein said propylene glycol is present in the amount of 20 to 70 weight %, said glycerin is present in the amount of 10 to 60 weight % and said water is present in the amount of 10 to 35 weight %, and wherein the composition is free of any other alcohol except propylene glycol and glycerin.

2. The stick-type deodorant base composition of claim 1, wherein said propylene glycol is present in the amount of about 30 to about 60 weight %.

3. The stick-type deodorant base composition of claim 1, wherein said propylene glycol is present in the amount of about 35 to about 50 weight %.

4. The stick-type deodorant base composition of claim 1, wherein said glycerin is present in the amount of about 10 to about 40 weight %.

5. The stick-type deodorant base composition of claim 1, wherein said glycerin is present in the amount of about 10 to about 30 weight %.

6. The stick-type deodorant base composition of claim 1, wherein said water is present in the amount of about 15 to about 40 weight %.

7. The stick-type deodorant base composition of claim 1, wherein said water is present in the amount of about 17 to about 29 percent weight %.

8. The stick-type deodorant base composition of claim 1, wherein said propylene glycol is present in the amount of about 43 to about 48 percent weight %, said glycerin is present in the amount of about 14 to about 23 percent weight % and said water is present in the amount of about 17 to about 28 percent weight %.

9. The stick-type deodorant base composition of claim 1, wherein said propylene glycol is present in the amount of about 47 to about 54 percent weight %, said glycerin is present in the amount of about 11 to about 22 percent weight % and said water is present in the amount of about 23 to about 28 percent weight %.

10. The stick-type deodorant base composition of claim 1, further comprising one or more soothing agents, one or more antioxidants, and optionally, one or more fragrances.

11. The stick-type deodorant base composition of any preceding claims, wherein the thickening agent is at least one material chosen from an alkali metal fatty acid salt, an alkaline earth metal fatty acid salt, an aluminum fatty acid salt, and an amine fatty acid salt, wherein the fatty acid is a $C_{14}$-$C_{22}$ fatty acid.

12. The stick-type deodorant base composition of claim 1, wherein said thickening agent comprises sodium stearate.

13. The stick-type deodorant base composition of claim 12, wherein said sodium stearate is present in the amount of about 3 to about 8 weight %.

14. The stick-type deodorant base composition of claim 1, wherein the composition has a payout of greater than about 0.35 g as measured on a payout test machine.

15. A stick-type deodorant base composition comprising:
a) an alcohol consisting of propylene glycol and glycerin;
b) a thickening agent in an amount so that the composition forms a deodorant stick; and
c) water;
wherein said propylene glycol is present in the amount of about 31 weight %, said glycerin is present in the amount of about 38 weight % and said water is present in the amount of about 14 weight %, and
wherein the composition is free of any other alcohol except propylene glycol and glycerin.

16. The stick-type deodorant base composition of claim 1, wherein the weight ratio of propylene glycol:water:glycerin is about 2:1:1.

17. The stick-type deodorant base composition of claim 1, wherein the deodorant base composition comprises one of the following:
a) 30.4 weight % propylene glycol, 16.4 weight % water, 47.1 weight % glycerin and 4 weight % sodium stearate;
b) 46.9 weight % propylene glycol, 16.4 weight % water, 30.1 weight % glycerin and 4 weight % sodium stearate;

c) 24 weight % propylene glycol, 20.8 weight % water, 47.1 weight % glycerin and 6 weight % sodium stearate;
d) 60 weight % propylene glycol, 16.6 weight % water, 14.3 weight % glycerin and 7 weight % sodium stearate;
e) 40.1 weight % propylene glycol, 40 weight % water, 10.8 weight % glycerin and 7 weight % sodium stearate;
f) 46.9 weight % propylene glycol, 22.5 weight % water, 22.5 weight % glycerin and 6 weight % sodium stearate;
g) 60 weight % propylene glycol, 24.1 weight % water, 10.8 weight % glycerin and 6 weight % sodium stearate;
h) 46.9 weight % propylene glycol, 24.5 weight % water, 22.5 weight % glycerin and 4 weight % sodium stearate;
i) 39 weight % propylene glycol, 32.5 weight % water, 22.5 weight % glycerin and 4 weight % sodium stearate;
j) 60 weight % propylene glycol, 20.1 weight % water, 10.8 weight % glycerin and 7 weight % sodium stearate;
k) 21.9 weight % propylene glycol, 32.5 weight % water, 37.5 weight % glycerin and 6 weight % sodium stearate;
l) 33.8 weight % propylene glycol, 24.9 weight % water, 34.2 weight % glycerin and 5 weight % sodium stearate;
m) 21.9 weight % propylene glycol, 32.5 weight % water, 40 weight % glycerin and 4 weight % sodium stearate;
n) 21.9 weight % propylene glycol, 22.9 weight % water, 47.1 weight % glycerin and 6 weight % sodium stearate;
o) 37 weight % propylene glycol, 32.5 weight % water, 24.5 weight % glycerin and 6 weight % sodium stearate;
p) 44.1 weight % propylene glycol, 40 weight % water, 10.8 weight % glycerin and 3 weight % sodium stearate;
q) 46.9 weight % propylene glycol, 20.8 weight % water, 24.2 weight % glycerin and 6 weight % sodium stearate;
r) 21.9 weight % propylene glycol, 24.9 weight % water, 47.1 weight % glycerin and 4 weight % sodium stearate;
s) 59 weight % propylene glycol, 22 weight % water, 10 weight % glycerin and 3-7 weight % sodium stearate;
t) 54 weight % propylene glycol, 28 weight % water, 47.1 weight % glycerin and 3-0 7 weight % sodium stearate; and
u) 30 weight % propylene glycol, 17.6 weight % water, 45 weight % glycerin and 3-7 weight % sodium stearate.

18. The stick-type deodorant base composition of claim 1, wherein the composition provides a zone of inhibition of at least 1 mm according to the Zone of Inhibition Test.

19. A method of inhibiting bacterial growth on skin comprising applying the composition of claim 1 to skin.

20. A stick-type deodorant comprising the stick-type deodorant base composition of claim 1 and one or more deodorancy agents.

21. The stick-type deodorant of claim 20 further comprising one or more soothing agents, one or more antioxidants and, optionally, one or more fragrances.

22. The stick type deodorant of claim 20, wherein said one or more deodorancy agents comprise one or more bactericides and/or bacteriostats.

* * * * *